US008500659B2

(12) United States Patent
Vastano

(10) Patent No.: US 8,500,659 B2
(45) Date of Patent: *Aug. 6, 2013

(54) METHOD FOR PHYSIOLOGICAL VOLUME MEASUREMENT AND ANALYSIS FOR BODY VOLUME VISUALIZATION

(76) Inventor: Gaetano F. Vastano, Kent, WA (US)

( * ) Notice: Subject to any disclaimer, the term of this patent is extended or adjusted under 35 U.S.C. 154(b) by 1244 days.

This patent is subject to a terminal disclaimer.

(21) Appl. No.: 11/703,566

(22) Filed: Feb. 7, 2007

(65) Prior Publication Data

US 2007/0135737 A1    Jun. 14, 2007

Related U.S. Application Data

(63) Continuation-in-part of application No. 10/390,491, filed on Mar. 17, 2003, now Pat. No. 7,201,726.

(51) Int. Cl.
*A61B 5/117*    (2006.01)
*A61B 5/103*    (2006.01)

(52) U.S. Cl.
USPC ........................................................ 600/587

(58) Field of Classification Search
USPC ........... 600/587, 592, 594, 507; 33/511–512; 702/156, 189; 73/149
See application file for complete search history.

(56) References Cited

U.S. PATENT DOCUMENTS

| 3,847,142 A | 11/1974 | Williams et al. |
| 5,891,059 A | 4/1999 | Anderson |
| 6,413,212 B1 | 7/2002 | Raab |

OTHER PUBLICATIONS

Lasinski et al, Comprehensive Lymphedema Management: Results of a 5-year follow-up, Lymphology 35 (Suppl):301-304, 2002.*
Vannier et al, Visualization of Prosthesis Fir in Lower-Limb Amputees, Sep.-Oct. 1997 (vol. 17, No. 5).*

* cited by examiner

*Primary Examiner* — Brian Szmal
(74) *Attorney, Agent, or Firm* — J. Wiley Horton

(57) ABSTRACT

A repeatable patient-specific measurement technique. The process employs common anatomical reference points to guide the individual performing the measurements. The measurements taken are logged into a database using a standard format. A volume corresponding to the area measured is then calculated. The series of measurements can be accurately repeated during subsequent evaluations of the individual. Subsequent volume calculations are also made so that the volume of the measured region can be tracked over time. The volumetric information is then used to evaluate certain individual-specific criteria such as efficacy of weight management plan. Computer software will also present the data in a variety of numerical and graphical formats that are useful to the individual.

8 Claims, 18 Drawing Sheets

☐ New
Patient Name: Joliet, Megan  83

Date: _____ 44
Time: _____

2/20/2003 12:00:00AM

Body Area 42    ☐ Affected Right Arm
                ☐

Measurements are in    Centimeters

| 40 Intervals | | Circumference Measurement |
|---|---|---|
| A - B | 3 | |
| B - C | 3 | |
| C - D | 1 | |
| D - E | 1 | |
| E - F | 1 | |
| F - G | 1 | |
| G - H | 1 | |
| H - I | 3 | |
| I - J | 3 | |
| J - K | 3 | |
| K - L | 3 | |
| L - M | 3 | |
| M - N | 3 | |
| N - O | 3 | |
| O - P | 3 | |
| P - Q | 3 | |
| Q - R | 3 | |
| R - S | 3 | |
| S - T | 3 | |
| T - U | 3 | |
| U - V | 3 | |

46

| Treatments | | |
|---|---|---|
| | Code | Duration (minutes) |
| Primary | | |
| Secondary | | |
| Third | | |
| Fourth | | |
| Fifth | | |

Notes 48

Patient Name: Joliet, Megan  Body Area: Affected Right Arm
Date of Measurement: 2/5/2003   7:49:09PM   Measurements are in Centimeters

| Point | Measurements | Circumference @ | | Unit of Measure Conversions Segmental Volume | Liters | Percent change from First Treatment % units | | | Previous Date |
|---|---|---|---|---|---|---|---|---|---|
| A | 0 cm. Distal end of ulna styloid process to axilla | 23.22 cm. | AB | 172.88 | 0.17 | -27.69 | -0.07 | Liters | 0.04 |
| B | 4.00 cm. Distal end of ulna styloid process to axilla | 23.39 cm. | BC | 137.10 | 0.14 | -37.40 | -0.08 | Liters | -1.86 |
| C | 8.00 cm. Distal end of ulna styloid process to axilla | 18.00 cm. | CD | 115.02 | 0.12 | -37.27 | -0.07 | Liters | -4.08 |
| D | 12.00 cm. Distal end of ulna styloid process to axilla | 20.00 cm. | DE | 143.56 | 0.14 | -26.39 | -0.05 | Liters | -2.05 |
| E | 16.00 cm. Distal end of ulna styloid process to axilla | 22.45 cm. | EF | 179.34 | 0.18 | -19.50 | -0.04 | Liters | -1.90 |
| F | 20.00 cm. Distal end of ulna styloid process to axilla | 25.00 cm. | FG | 232.47 | 0.23 | -8.84 | -0.02 | Liters | -3.08 |
| G | 24.00 cm. Distal end of ulna styloid process to axilla | 29.00 cm. | GH | 267.70 | 0.27 | -16.48 | -0.05 | Liters | -3.03 |
| H | 28.00 cm. Distal end of ulna styloid process to axilla | 29.00 cm. | HI | 306.32 | 0.31 | -29.06 | -0.13 | Liters | -2.49 |
| I | 32.00 cm. Distal end of ulna styloid process to axilla | 33.00 cm. | IJ | 366.98 | 0.37 | -29.20 | -0.15 | Liters | -2.26 |
| J | 36.00 cm. Distal end of ulna styloid process to axilla | 34.90 cm. | JK | 366.98 | 0.37 | -30.91 | -0.16 | Liters | -2.99 |
| K | 40.00 cm. Distal end of ulna styloid process to axilla | 33.00 cm. | KL | 336.24 | 0.34 | -26.76 | -0.12 | Liters | -3.48 |
| L | 44.00 cm. Distal end of ulna styloid process to axilla | 32.00 cm. | LM | 326.97 | 0.33 | -22.70 | -0.10 | Liters | -2.78 |
| M | 48.00 cm. Distal end of ulna styloid process to axilla | 32.10 cm. | MN | 316.88 | 0.32 | -26.69 | -0.12 | Liters | -2.49 |
| N | 52.00 cm. Distal end of ulna styloid process to axilla | 31.00 cm. | NO | 316.88 | 0.32 | -28.27 | -0.12 | Liters | -2.49 |
| O | | 32.10 cm. | OP | | | | | | |
| P | | | PQ | | | | | | |
| Q | | | QR | | | | | | |
| R | | | RS | | | | | | |
| S | | | ST | | | | | | |
| T | | | TU | | | | | | |
| U | | | UV | | | | | | |
| V | | | Total Volume | 3,585.32 cubic cm | 3.59 Liters | -26.41 % | -1.29 Liters | | -2.58 % |

Notes

Ms. J indicated her arm feels stronger. She has been wearing the compression wraps and feel that they are helping

52

Treatments

| Category | Treatments | Duration(min) |
|---|---|---|
| Primary | 97110 | 40 |
| Secondary | 97535 | 30 |
| Third | 97112 | 25 |
| Fourth | 97140 | 15 |
| Fifth | 97150 | 10 |

FIG.10

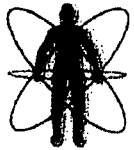

*Quantitative Volumetric Outcome Report*

Report Date: 2/20/2003

| Patient Name: | Joliet, Megan | Social Security Number: | 064-45-3121 |

Sex: Female
Age: 55
Home Phone: (212) 333-1444
Work Phone: (212) 666-1313 ext. 67
Race: Hispanic or Latino
Ethnicity: Hispanic or Latino
Physicians:

Occupation: 654
Initial eval date: 1/27/2003
Surgery Date: 1/30/2003
Therapists:
  Taylor, Cynthia Diagnosis:
675.45

Primary Insurance:   Secondary Insurance
Blue Cross

Report Data Selection Criteria

All patient measurements for the selected body part, Affected Right Arm

This patient was treated for 7 sessions

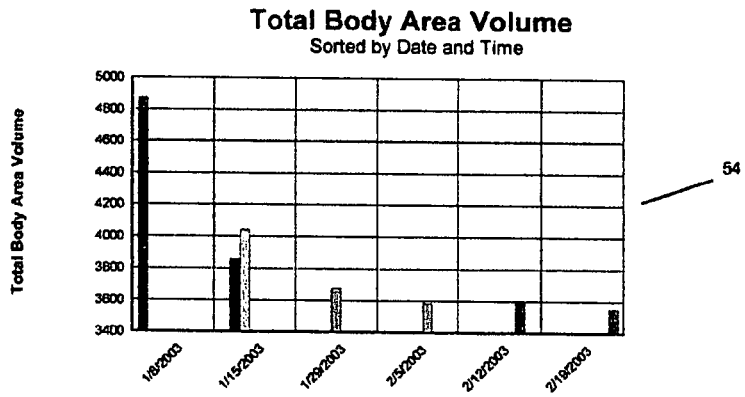

*Volumes*
 ver 1.0

FIG. 11

| | 01/30/07 |
|---|---|
| Date: | |
| Blood Pressure: | 140/85 |
| Body Fat %: | 35.00 |
| Weight: | 252.00 |
| Height: | 73.00 |
| BMI: | 33.20 |
| Daily Caloric: | 3,200.00 |
| Exercise: | 25.00 |
| Resting HR: | 82.00 |

| Measurements | Circumference (Inches) | Sectional Volume (Cubic inches) | Measurements | Circumference (Inches) | Sectional Volume (Cubic inches) |
|---|---|---|---|---|---|
| RL - Right Leg | | | LL - Left Leg | | |
| Right Leg_2 | 9.45 | 65.85 | Left Leg_2 | 9.45 | 67.51 |
| Right Leg_3 | 16.00 | 96.85 | Left Leg_3 | 16.30 | 97.51 |
| Right Leg_4 | 15.20 | 109.90 | Left Leg_4 | 15.00 | 110.66 |
| Right Leg_5 | 18.00 | 172.32 | Left Leg_5 | 18.30 | 178.36 |
| Right Leg_6 | 23.50 | 222.55 | Left Leg_6 | 23.92 | 228.42 |
| Right Leg_7 | 23.80 | | Left Leg_7 | 24.00 | |
| Total | | 667.47 | Total | | 682.46 |
| W - Waist | | | C - Chest | | |
| Waist_1 | 42.30 | 728.04 | Chest_2 | 47.20 | 812.10 |
| Waist_2 | 43.25 | 734.51 | Chest_3 | 53.75 | |
| Waist_3 | 42.68 | 747.43 | Total | | 812.10 |
| Waist_4 | 44.00 | | | | |
| Total | | 2209.98 | | | |
| H - Head | | | N - Neck | | |
| Head_1 | 22.90 | 74.68 | Neck_1 | 18.35 | 53.24 |
| Head_2 | 20.40 | | Neck_2 | 18.23 | |
| Total | | 74.68 | Total | | 53.24 |
| RF - Right Foot | | | LF - Left Foot | | |
| Right Foot_1 | 9.20 | 15.95 | Left Foot_1 | 9.50 | 15.45 |
| Right Foot_2 | 10.80 | | Left Foot_2 | 10.20 | |
| Total | | 15.95 | Total | | 15.45 |
| RA - Right Arm | | | LA - Left Arm | | |
| Right Arm_2 | 6.50 | 14.51 | Left Arm_2 | 6.50 | 14.08 |
| Right Arm_3 | 7.00 | 31.92 | Left Arm_3 | 6.80 | 31.08 |
| Right Arm_4 | 12.75 | 58.07 | Left Arm_4 | 12.67 | 57.08 |
| Right Arm_5 | 14.25 | 76.64 | Left Arm_5 | 14.10 | 73.42 |
| Right Arm_6 | 16.75 | 94.58 | Left Arm_6 | 16.25 | 92.05 |
| Right Arm_7 | 17.72 | | Left Arm_7 | 17.75 | |
| Total | | 275.72 | Total | | 267.71 |

FIG. 14

METHOD FOR PHYSIOLOGICAL VOLUME MEASUREMENT AND ANALYSIS FOR BODY VOLUME VISUALIZATION

CROSS-REFERENCES TO RELATED APPLICATIONS

This is a continuation in part of U.S. application Ser. No. 10/390,491 filed Mar. 17, 2003 now U.S. Pat. No. 7,201,726 which names the same inventor.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of health and wellness. More specifically, the invention comprises a method for accurately calculating the volumes of portions of an individual's body, and using the calculated volumes to visually track changes in body appearance over time using a computer generated representation of the individual's body volume.

2. Description of the Related Art

In assessing and monitoring the efficacy of weight and exercise programs, it is often helpful to know the volume of a portion or portions of the body. Many weight and exercise programs produce results that are not directly quantified as weight loss. For example, a diet of increased protein with weight training may lead to weight gain but an overall reduction in body volume. An individual may also lose body volume in a certain area but increase volume in another while experiencing a weight loss. Understanding and visualizing the dynamic changes in volume and correlating them to weight changes can assist an individual in understanding and maximizing the effectiveness of a particular weight and exercise program. More efficient and individual specific programs can be developed by understanding an individual's response to certain types of dietary and exercise programs.

An individual commonly uses his or her body weight as a means to gauge overall health and wellness. Individuals also often use the measurement of weight change to evaluate the efficacy of certain dietary and exercise programs. Observations of weight alone do not accurately convey the entire state of an individual's results with regard to a specific dietary and exercise program, however.

To properly document the progress of dietary and exercise programs it is often necessary to evaluate factors such as volumetric changes over time. It is very difficult to repeat one or two measurements taken of a particular location, since they may not be tied to a convenient anatomical reference. Thus, the traditional approaches may not be able to provide repeatable results even in terms of a qualitative change over time. If, as an example, an individual measures the diameter of his or her forearm between the wrist and the elbow, it may be difficult to accurately repeat the position of the measurement when the individual measures the forearm a week later. If a different diameter is then observed, the individual will not know whether it represents a change in weight or merely an artifact of the measurement process.

Accordingly, it would be desirable to provide a measurement and volume calculation technique that is easily repeatable and accurately estimates the volumes of various portions of an individual's body. It would also be desirable to have a tool that may be used to correlate the volumetric data of an individual to certain factors affecting the individual's exercise and health management program. It would also be desirable for this tool to provide a computer-generated representation of the individual's body volume to aid the individual in understanding and visualizing the dynamic changes in volume.

BRIEF SUMMARY OF THE INVENTION

The present invention comprises a repeatable patient-specific measurement technique, along with a technique for analyzing and visualizing the data obtained. The inventive process employs common anatomical reference points to guide the individual performing the measurements. The measurements taken are logged into a database using a standard format. A volume corresponding to the area measured is then calculated. The series of measurements can be accurately repeated during subsequent evaluations of the same individual. Subsequent volume calculations are also made so that the volume of the measured region can be tracked over time. The volumetric information is then used to evaluate certain individual-specific criteria such as efficacy of weight loss and exercise programs and the relationship of body part and whole body volume to the overall analysis of the efficacy of those programs. The volumetric information is correlated to (1) the individual's specific exercise routines, (2) dietary consumption including food categories and calories consumed, (3) region of origin, (4) age, (5) sex, (6) ethnicity, (7) occupation, (8) Body Mass Index (BMI), (9) blood pressure, (10) body fat percentage, (11) resting heart rate, and (12) weight in order to evaluate the efficacy of dietary and exercise programs.

The process is preferably performed using computer software to record the measurement techniques, calculate the volumes, calculate the BMI and present the data in a variety of numerical and graphical formats. The creation of volumetric self-image on the compacter allows for visual representation of the data over time. The individual can visually see changes in body volume in relationship to their specific dietary and exercise programs.

BRIEF DESCRIPTION OF THE SEVERAL VIEWS OF THE DRAWINGS

FIG. 10 is a view of a sample data sheet.

FIG. 11 is a view of a sample graphical presentation of the data.

FIG. 14 is a data input display, showing measurement data input into a computer.

REFERENCE NUMERALS IN THE DRAWINGS

| | | | |
|---|---|---|---|
| 10 | centerline | 12 | external start point |
| 14 | faceted volume | 16 | arm |
| 18 | ulna styloid process | 20 | axilla |
| 28 | atypical leg | 30 | computed volume |
| 32 | lower plane | 34 | upper plane |
| 36 | measurement input form | 38 | physiological reference |
| 40 | length input | 42 | circumference input |
| 44 | date/time entry | 46 | treatment input |
| 48 | notation input | 50 | measurement guide |
| 52 | sample data sheet | 54 | graphical data presentation |
| 60 | chord length | 62 | contoured object |
| 64 | reference model | 66 | health data |
| 68 | circumference data | 70 | computed volume data |
| 72 | three-dimensional representation | 74 | comparison data |
| 76 | three-dimensional representation | 78 | three-dimensional representation |
| 80 | comparison data | | |
| C1 | first circumference | C2 | second circumference |
| C3 | third circumference | C4 | fourth circumference |
| C5 | fifth circumference | C6 | sixth circumference |
| C7 | seventh circumference | C8 | eighth circumference |
| C9 | ninth circumference | C10 | tenth circumference |
| L1 | first length | L2 | second length |
| L3 | third length | L4 | fourth length |
| L5 | fifth length | V1 | first volume |
| V2 | second volume | V3 | third volume |
| V4 | fourth volume | V5 | fifth volume |
| V6 | sixth volume | V7 | seventh volume |
| V8 | eighth volume | V9 | ninth volume |

DETAILED DESCRIPTION OF THE INVENTION

Figure 1:
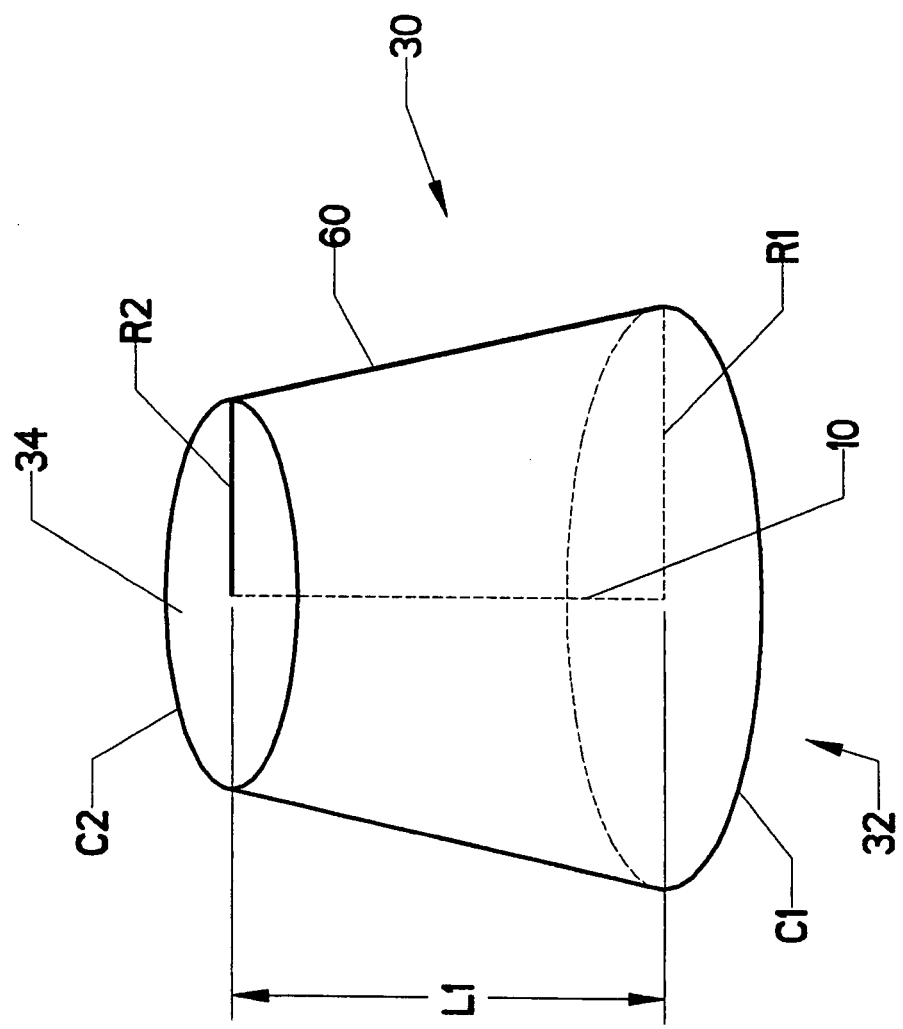
FIG. 1 is an isometric view, showing a truncated cone.

FIG. 1 shows the basic geometrical element used in the present invention—a truncated right cone. This object is defined by lower plane 32, having first circumference C1, and upper plane 34, having second circumference C2. Upper plane 34 is offset from lower plane 32 a first length L1 along central axis 10. The radius corresponding to each circumference can be found using the following expression $R=C/(2\times\Pi)$ where "C" represents the circumference and "R" represents the corresponding radius.

A radius R1 corresponding to first circumference C1 and a radius R2 corresponding to second circumference C2 are thereby computed. The volume of the truncated cone can then be determined using the expression:

$$V = \frac{1}{3} \times \Pi \times L1 \times (R1^2 + R2^2 + R1 \times R2)$$

Thus, by knowing the values for C1, C2, and L1, one can easily determine a value for computed volume 30. These geometric principles are essential to the inventive process herein disclosed, for the simple truncated cone can be used to approximate many types of complex geometry.

Figure 2:
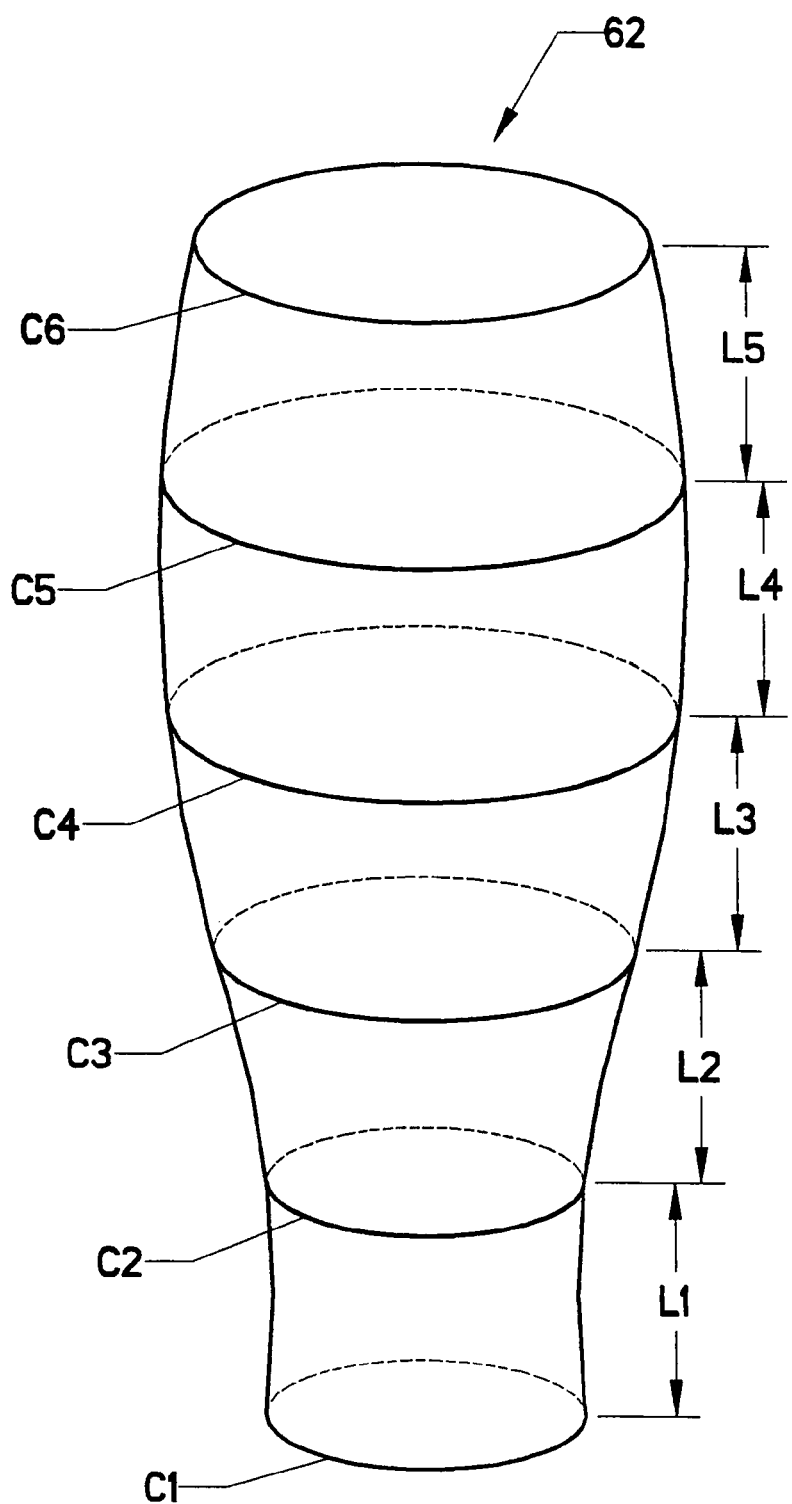
FIG. 2 is an isometric view, showing an example of contoured geometry.

FIG. 2 depicts contoured object 62, which has a complex curved shape. Like the truncated cone of FIG. 1, it has a central axis. In order to determine its volume, the user first selects an external start point. A circumference measurement—C1—is taken at this point. The user then moves along the object's surface, in a direction approximately perpendicular to the first circumference measurement taken, a distance L1. A second circumference measurement—C2—is then taken. This process continues with the user recording the values for L1 through L5 and for C1 through C6. The software tracks variability in the step size as set forth in the patient-specific measurement technique (explained in more detail subsequently).

Figure 3:
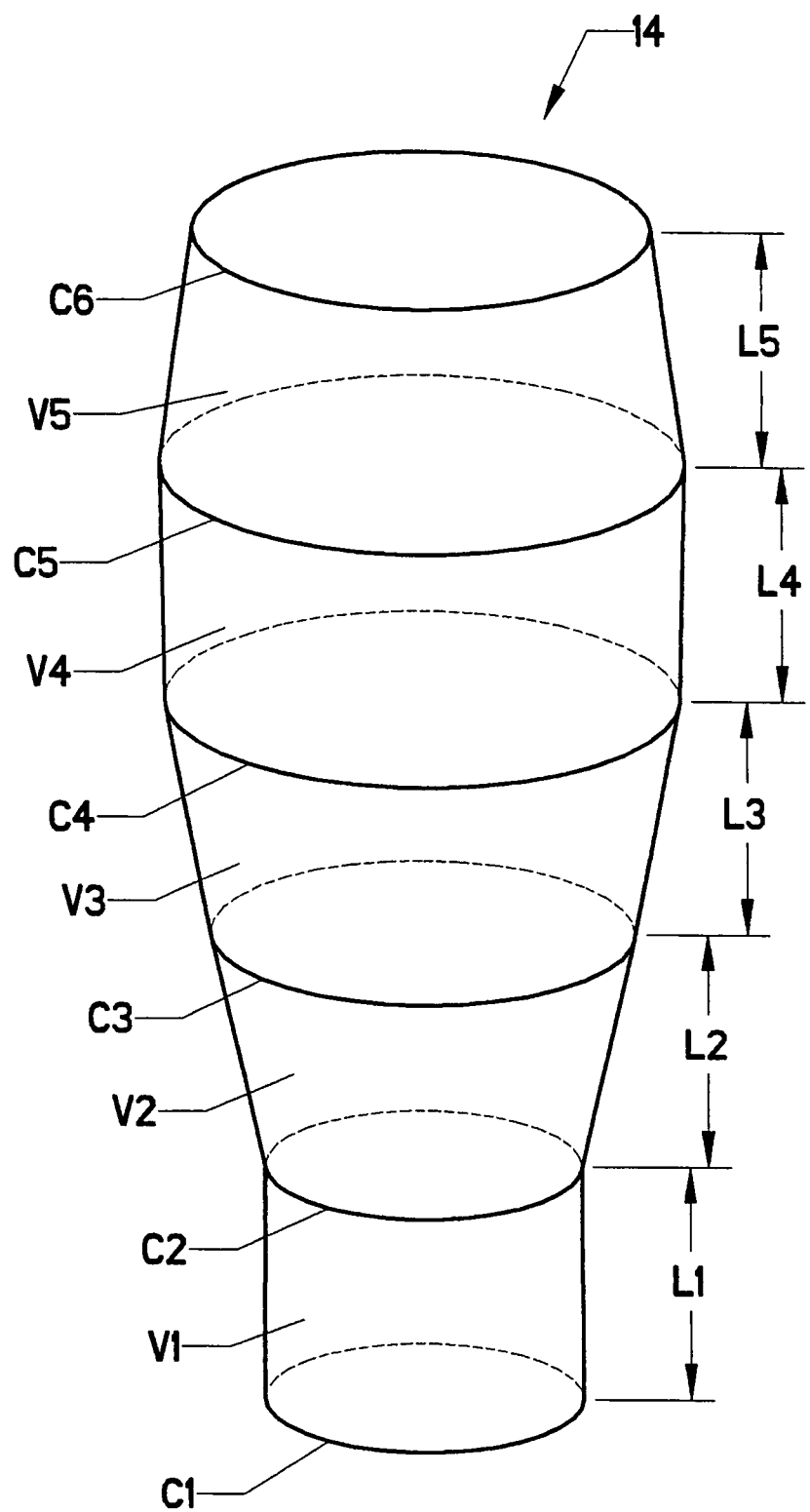
FIG. 3 is an isometric view, showing an example of faceted geometry.

FIG. 3 represents graphically the measurements taken from contoured object 62 in FIG. 2. The regions between the circumference measurements are linearly interpolated to form a stack of truncated cones, each one of which is similar to the one shown in FIG. 1 (denoted as first volume V1 through fifth volume V5). The stack of truncated cones is referred to collectively as faceted volume 14.

Using the same mathematical principles disclosed with respect to the truncated cone of FIG. 1, the volume of volumes V1 through V7 can be calculated. These volumes are then added to find the total volume for faceted volume 14.

Those skilled in the art will know that the volume thus determined is only an approximation of the true volume of contoured object 62. However, if the approach is properly applied, the error will be very small. Of equal significance, since the same technique will be applied during the patient's next visit, any error present will remain relatively constant. Thus, recorded changes will not be the result of variations in the measurement error.

It is customary in the field of mathematical modeling to refer to the distance between each circumference measurement as a "step size." The user taking the measurements can adjust the step size to increase accuracy. Obviously, a smaller step size produces greater accuracy. However, since the measurements are typically taken by hand, a small step size results in much more work. An experienced user can adjust the step size by using small steps in regions where the object's surface is rapidly changing, and larger step sizes in regions where the surface is not rapidly changing. Computer software can be used to track and "remember" a custom step size for a particular patient and body area.

Figure 4:
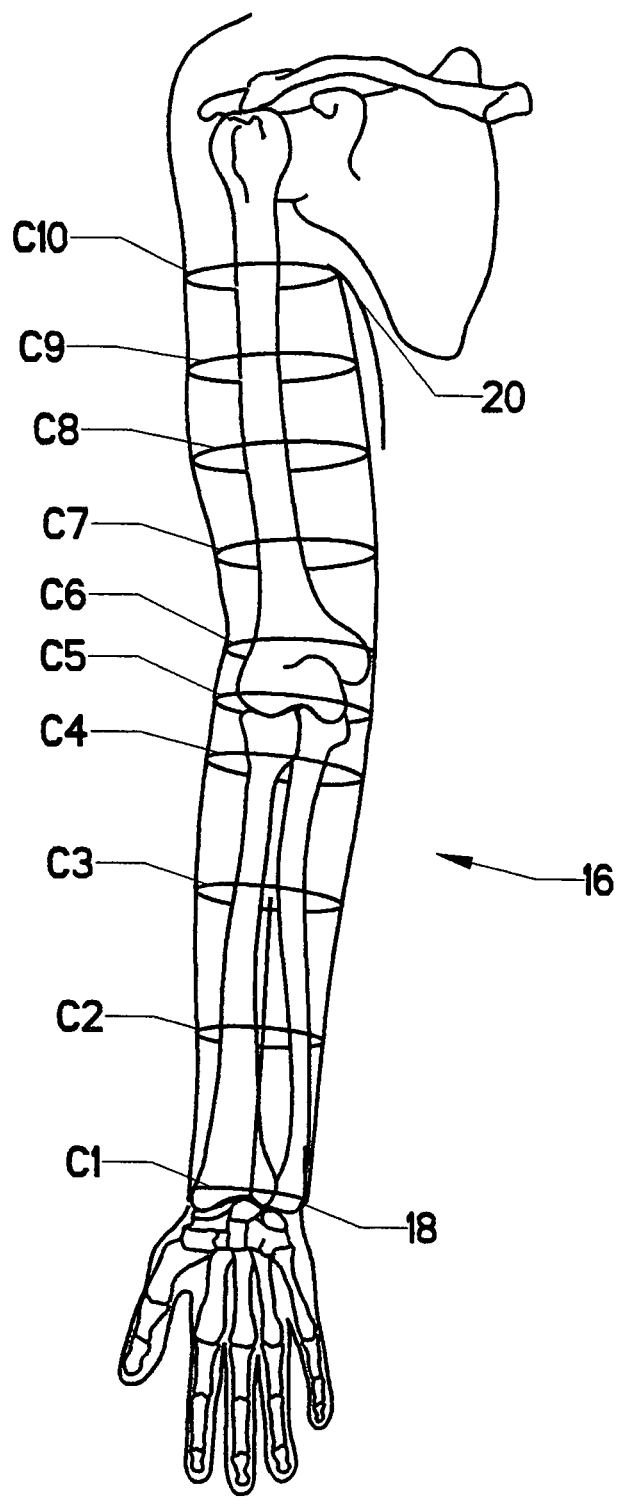
FIG. 4 is a perspective view, showing the application of the present process.

The application of the process to the human body will now be disclosed in detail. FIG. 4 shows the larger structures of arm 16. One key to the proper application of the inventive process is the selection of an anatomical reference point as the origin of the measurements taken. In the case of the human arm, one such reference point is ulna styloid process 18 (other features can be used as a reference on the arm). This feature is a knobby protrusion of the end of the ulna. It can be consistently identified by feeling around the patient's wrist.

Figure 6:
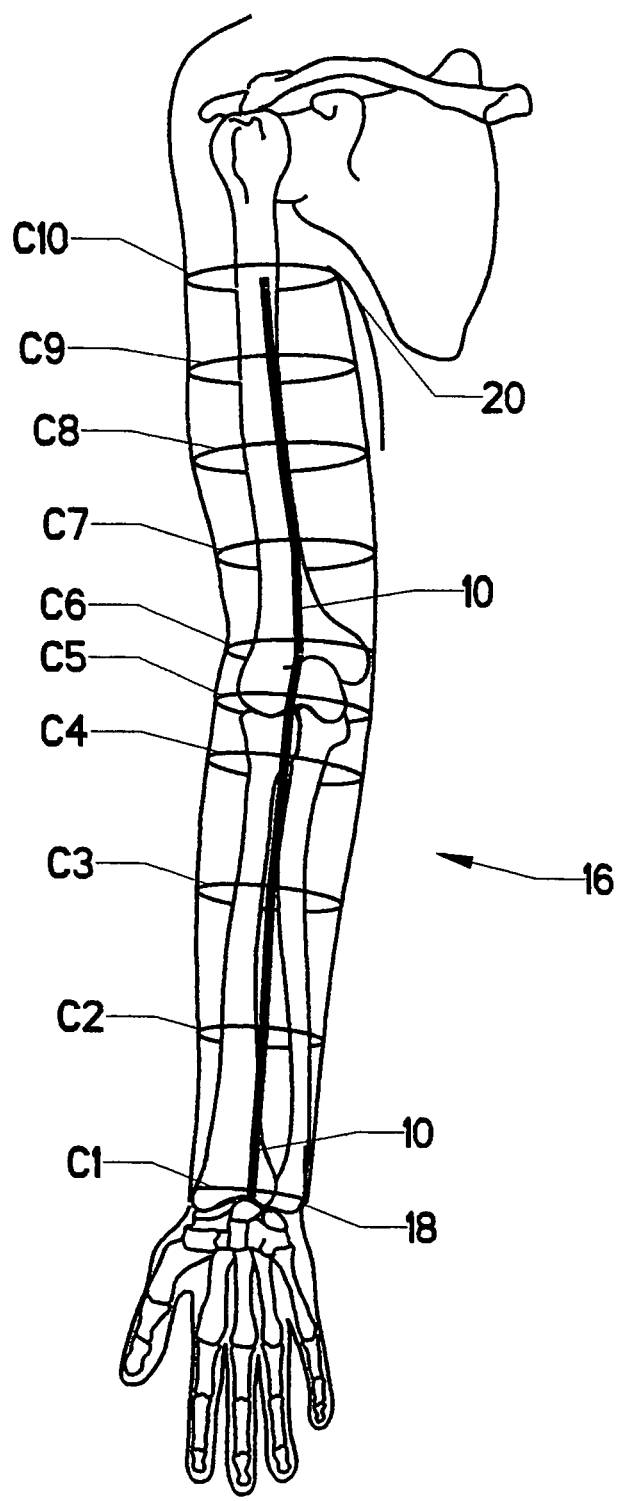
FIG. 6 is a perspective view, showing the application of the present process.

The process allows an individual to develop a measurement technique, which defines the anatomical references for the individual and assigns a centerline from which the step size will be initiated along the body part. The individual can deviate the centerline to follow the anatomical contours. FIG. 6 shows centerline 10 as it is adjusted to follow the contours of arm 16. The reader will observe that its course deviates significantly.

In this particular example, the measurements will be taken up to the individual's axilla 20. Returning to FIG. 4, the user begins by measuring first circumference C1. The user then moves up the arm a distance L1 and measures a value for second circumference C2. The user repeats this process for circumferences C3 through C10. The reader will note that the step size has been varied in the course of the measurements. This example represents measurements taken by an individual having experience using the measurement techniques described herein. The step size has been reduced in the vicinity of the elbow, where the surface geometry of the arm changes rapidly.

Figure 5:
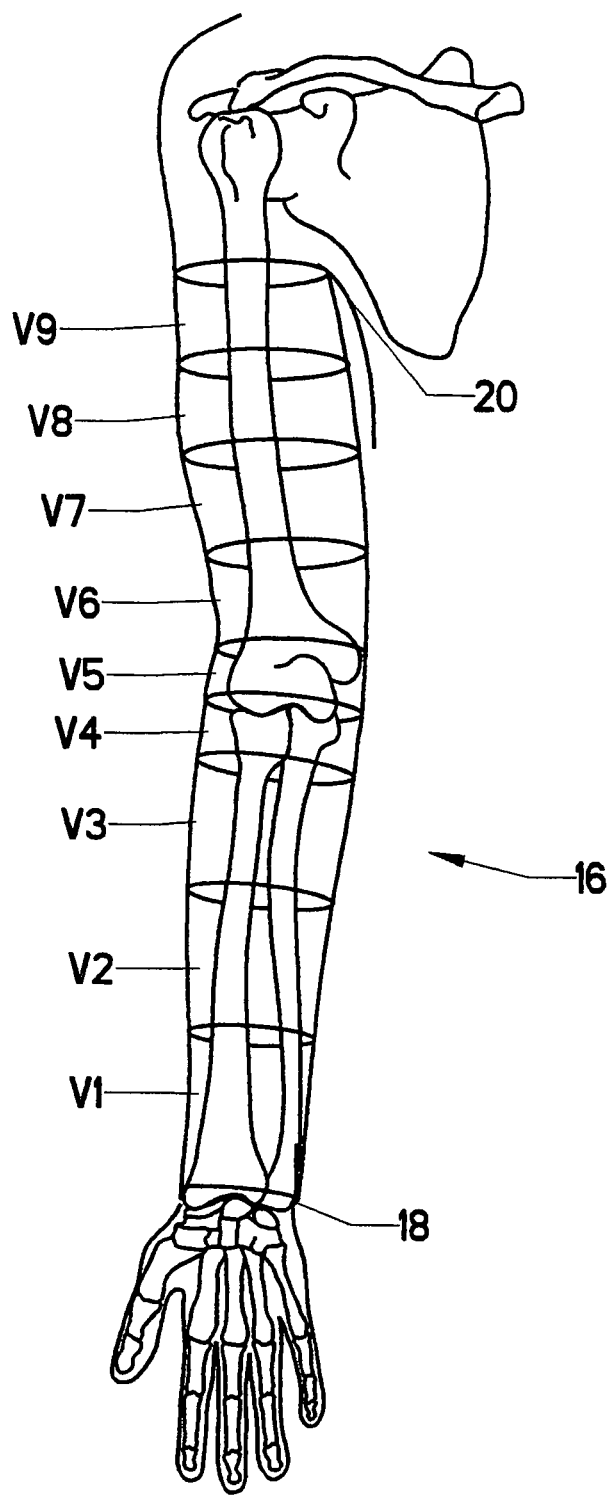
FIG. 5 is a perspective view, showing the application of the present process.

Turning now to FIG. 5, the measurements taken have divided arm 16 into nine discrete volumes—volume V1 through volume V9. The reader will recall that the prior examples used volumes having a central axis; i.e., volumes that were radially symmetric. The human arm is obviously not radially symmetric, nor does its centerline follow a straight path. In FIGS. 4 through 6, it is apparent that the planes defined by the circumference measurements are not parallel. This fact introduces error into the volume calculations. It is therefore advisable to refine the process somewhat.

FIG. 6 shows the deviations in centerline 10. It graphically depicts a single circumference measurement being taken at the end of each linear segment of centerline 10. The reader will observe that a circumference measurement is taken at the intersection of each linear segment of centerline 10. The use of a single circumference measurement is non-optimal, since such a circumference is not generally perpendicular to both line segments it is adjacent to.

Figure 6B:
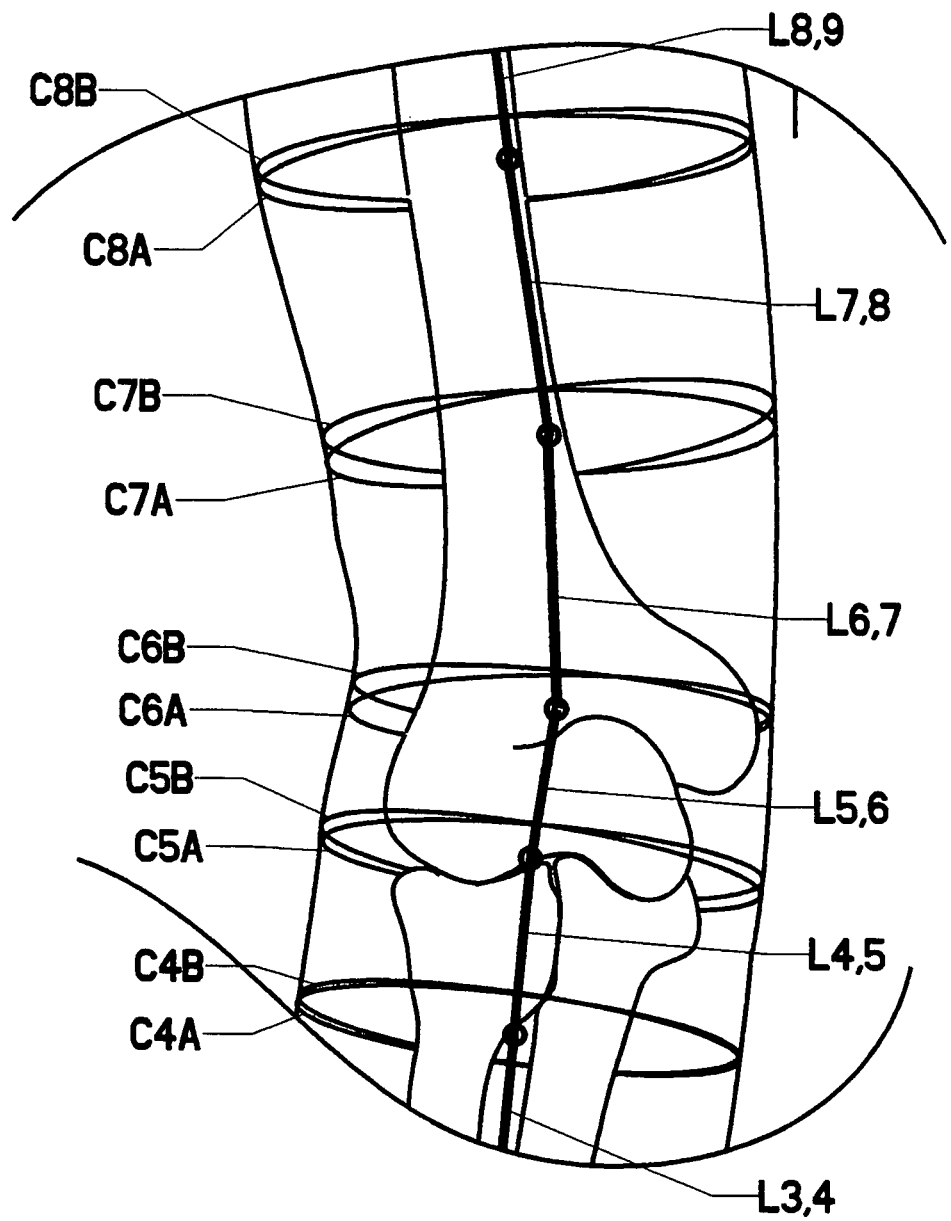
FIG. 6B is a detailed perspective view, showing the application of the present process.

FIG. 6B shows a refinement intended to address this concern. The reader will again observe that centerline 10 is broken into a series of non-aligned linear segments (labeled as "L3,4", "L4,5", and so on). At each intersection point between two segments, it is preferable to take two circumference measurements. For example, at the joint between segment L3,4 and segment L4,5, circumference measurements C4A and C4B are taken. C4A is perpendicular to L3,4 and C4,B is perpendicular to L4,5.

Figure 7:
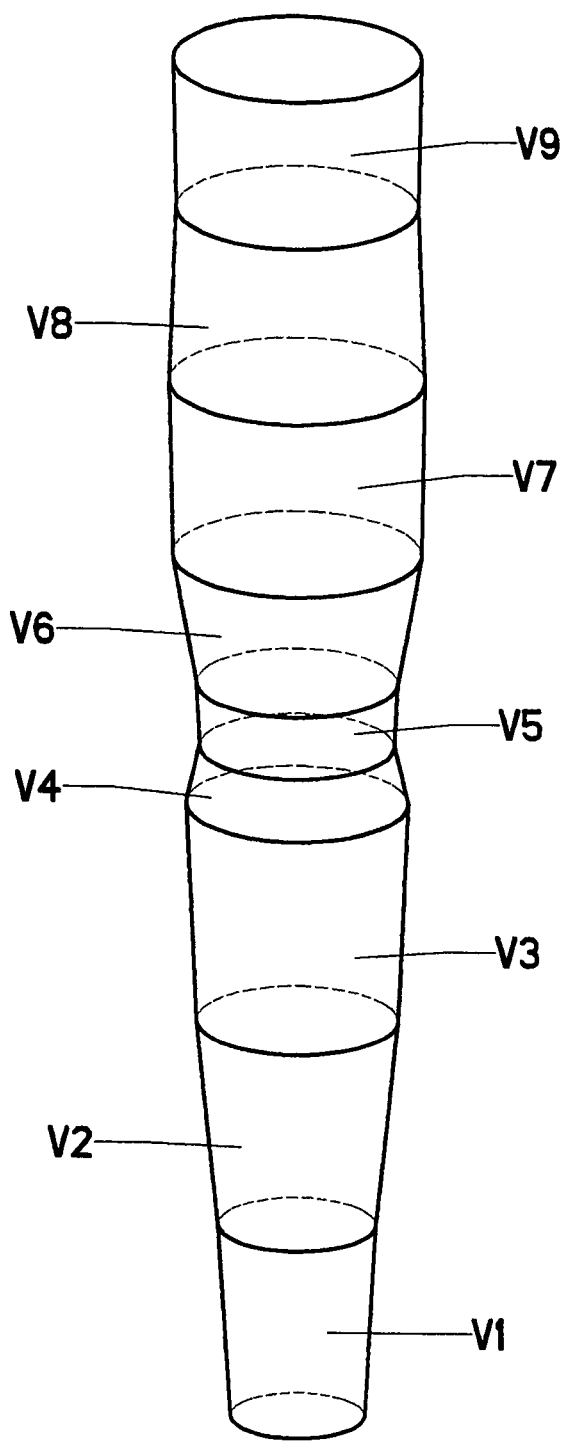
FIG. 7 is an isometric view, showing faceted geometry corresponding to the measurements of a limb.

This approach is easier to see graphically in the two circumference measurements indicated as C6A and C6B (since the centerline deviates its course more radically at that junction). C6A is perpendicular to L5,6, whereas C6B is perpendicular to L6,7. Using this approach, each truncated cone is defined by a linear segment of centerline and two circumference measurements, which are perpendicular to that linear segment. As an example, the volume corresponding to L6,7 is calculated using the length L6,7 and circumference measurements C6B and C7A. Thus, it is a true right cone. Error is thereby reduced and any error which is present is maintained more consistently over successive measurements. FIG. 7 shows the results of this approach applied to the entire arm. The arm has been segmented into volumes V1 through V9, with each volume comprising a true truncated right cone.

Figure 8:
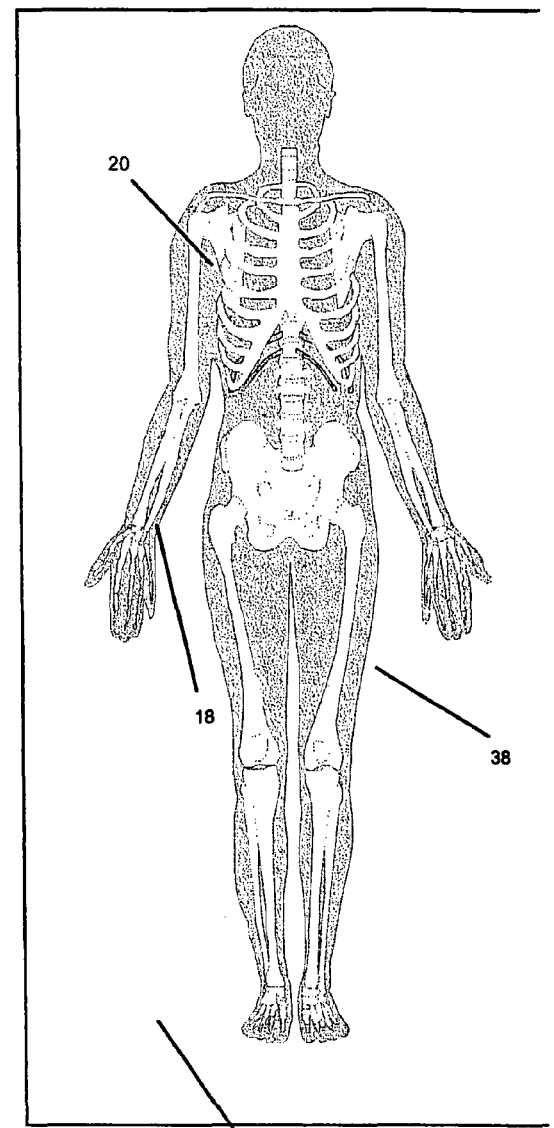
FIG. 8 is a view of a measurement input form.

One useful function of the process it to allow the individual to evaluate changes in the volume of a portions of the individual's body and total body volume over time. The individual may also correlate these volume changes to the individual's weight, BMI, calorie consumption, body fat percentage, resting heart rate, blood pressure and exercise program. Thus, the process contemplates that the measurements described will be repeated over two or more evaluations. Although this entire process can be carried out manually, the use of computer software is obviously advantageous in ensuring greater reliability and reproducibility of the data and the incorporation of other factors into data interpretation. In addition, the ability to graphically depict representations of the user's total body volume over time greatly enhances the individuals understanding of the relationship between body volume and the user's specific weight management and/or exercise programs. FIG. 8 depicts a user assistance printout from a computer program intended to aid the individual in carrying out the process (measurement input form 36).

The user selects a body area to evaluate, typically using choices from a pull-down menu. There is no restriction on the body area that can be selected. As examples, the software allows selection of both hands, feet, arms, legs, buttocks, torso, chest, neck, and head. The software displays an image of the selected limb specific to the sex of the patient.

To correspond with the illustrations of FIGS. 4 through 7, the patient's right arm has been selected. The program then graphically depicts suggested anatomical references on physiological reference 38. The user makes certain "picks" to inform the program of which reference points will be used. The user preferably also enters correlative data, such as date/time entry 44, treatment input 46 (describing the history of treatment), and notation input 48 (allowing the addition of observational or other notes).

The user then performs the measurement procedure described previously, entering the values observed as length inputs 40 and circumference inputs 42. The use of the computer program allows the addition of helpful instructions, a graphical depiction of the progress of the measurements along physiological reference 38, and error cross-checking to make sure that the recorded number of lengths and circumferences make sense. The error checking can also evaluate the numbers to detect possible mis-measurements (such as when one circumference is drastically shorter than its neighbors).

Figure 9:
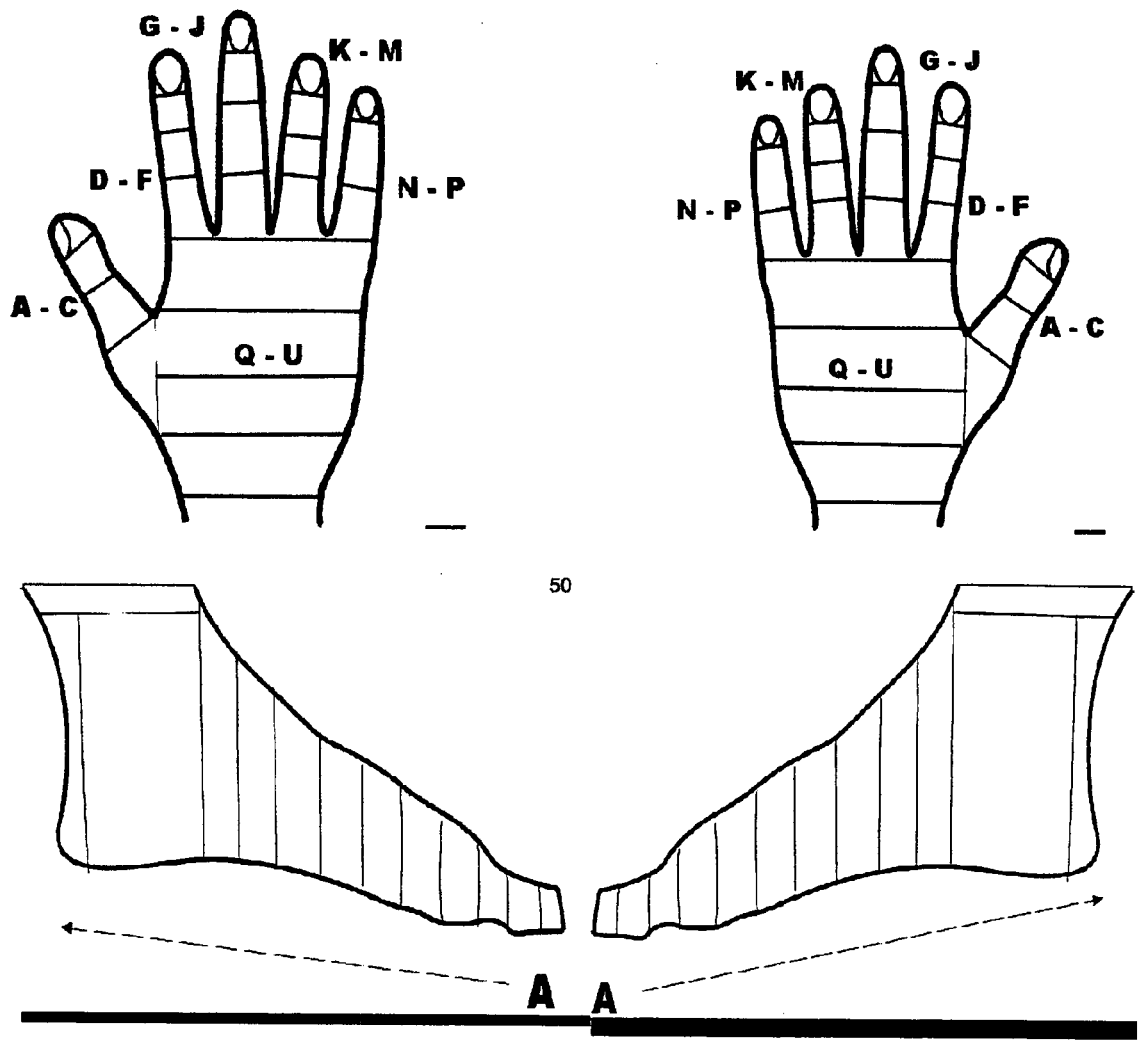
FIG. 9 is a view of a typical measurement guide.

FIG. 9 depicts another helpful display which can be generated by the computer program. If the user has selected a hand or foot to measure, this particular measurement guide 50 can be displayed. Custom intervals or step sizes are also tracked in this software feature. An unlimited number of intervals for all body areas can be tracked.

FIG. 10 shows a display of sample data sheet 52, which displays the data obtained by measuring a patient's arm. Such data sheets would be produced for a series of successive daily measurement sessions. Data sheets present the individualized measurement model created by the individual, circumference values at patient-specific points, sectional volumes, sectional percent change from previous sessions, sectional percent change from first session, conversion of sectional and total volumes to liters or gallons, total measured body area volumes and total measured body area volumes percent change from previous session and from first session. The sheet can also display graphical representations of the volumetric self-image, weight, BMI, daily calories consumed, daily exercise, blood pressure, percent body fat, heart rate and various graphical illustrations. Those skilled in the art will realize that these functions are merely exemplary. Many more could be added.

While it is possible to evaluate volumetric changes using the sample data sheets 52, it may aid understanding to present such data graphically. Again, the use of a computer program can provide this functionality. FIG. 11 shows graphical data presentation 54. This display presents an exemplary graphical "bar chart" showing volumetric changes of a particular individual over time. Those that are skilled in the art know that such a display could also be used to show changes in the individual's weight, BMI, blood pressure, percent body fat, resting heart rates, and daily calories consumed over time as well. Such a display allows the individual to easily evaluate the efficacy of a diet or exercise program. Such a display also helps the reader understand why the absolute accuracy of the volume calculation is not nearly as important as the repeatability of the measuring process and it relationship to changes in the weight and wellness factors.

The absolute volume taken on a first evaluation of an individual is not particularly instructive, as variations in human anatomy produce a wide range of volumes for a particular body part. The individual is much more interested in observing changes in the volume over the course of time in relationship to the individual's overall body weight, blood pressure, resting heart rate, percent body fat, BMI, daily calories consumed and daily exercise program. Most importantly, the individual needs to be confident that the changes seen are real and not an artifact of the measurement process. The repeatability of the inventive process herein disclosed greatly reduces the risk of artifact.

Figure 12:
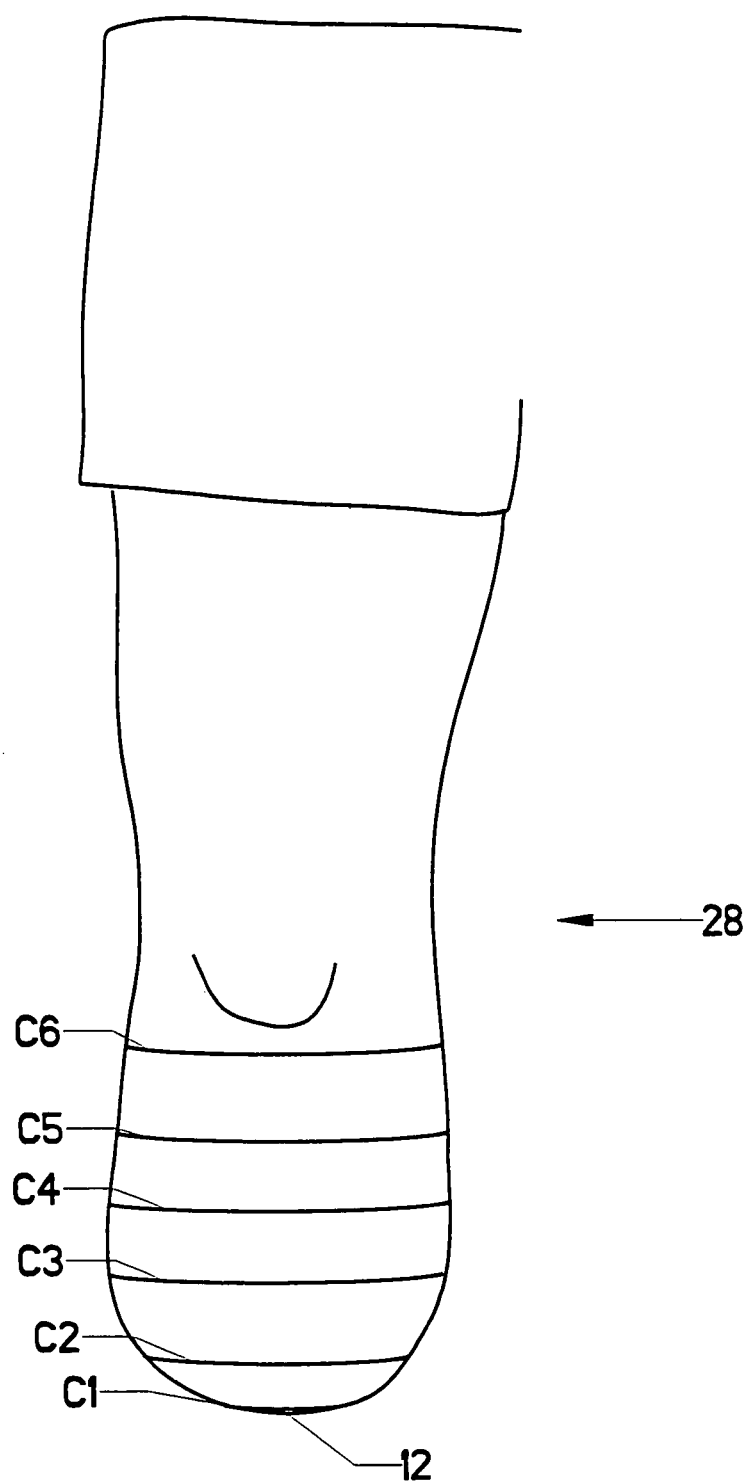
FIG. 12 is an isometric view, showing an atypical limb.
Figure 13:
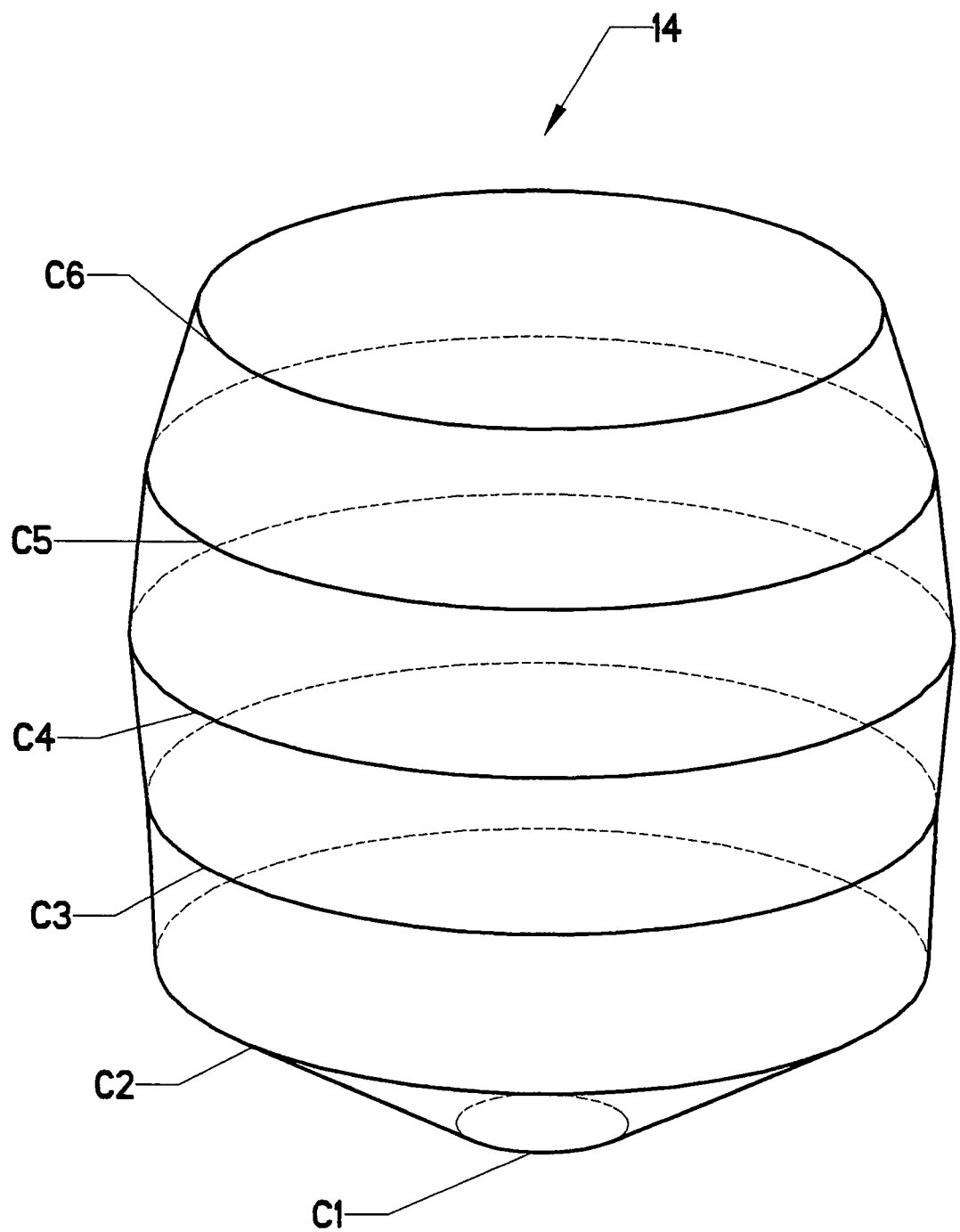
FIG. 13 is an isometric view, showing faceted geometry corresponding to the measurements of the atypical limb.

Further, the process can be employed to measure virtually any type of geometry, even where the patient's anatomy is atypical. FIG. 12 shows a patient having atypical leg 28 (a below-the-knee amputation). The same general process is employed. External starting point 12 is placed at the lower extreme (as may, for example, be recommended by the computer program). A series of circumference measurements C1 through C6 are then taken. These are then used to create faceted volume 14 as shown in FIG. 13. Thus, the reader will appreciate that the inventive process disclosed can be used for virtually any portion of human physiology. The reader will also appreciate that the process can be used to determine the volume of the human body as a whole.

The use of computer software allows the conversion of sectional and total volumes to liters or gallons, a comparison of section volume to total body volume, comparisons of total body weight, BMI, blood pressure, percent body fat, resting heart rate, daily calories consumed and relationship to daily exercise programs and numerous other mathematical operations. The software can even guide the individual to compare his or her data against similar populations of individuals based upon age, sex, occupation, geographic origin and the like. This type of analysis is valuable when evaluating the efficacy of a weight and health management program. Thus, the software can ask the individual to contribute data, which is needed for a populations study—even though the individual may not be directly aware of the study.

These circumference and fixed distance measurements may also be used by a computer to generate and display the volume of the individual as a graphical three-dimensional representation of the individual's physical form. In the preferred embodiment, this is accomplished by applying the circumference measurements to a standardized three-dimensional mesh representation of a human figure. As such, the circumference measurements are used to "refine" the standardized three-dimensional mesh representation to resemble the unique appearance of the individual. Such a process may be used to generate reports exemplified in FIGS. 15-17 as will be explained in greater detail subsequently.

Turning now to FIG. 14, a data input display for inputting measurement data in the computer is illustrated. The current data input display appears as a graphical user interface on the user's computer. Health data 66 is first input into the computer. Health data 66 includes the date, the individual's blood pressure, body fat percentage, weight, height, average daily caloric intake, daily exercise time, and resting heart rate. BMI is calculated from the individual's height and weight. Circumference data 68 is then input into the appropriate fields. Reference model 64 may be provided on the data input display to assist the user in identifying where circumference measurements should be made. In the present example, the variable fixed distances between the circumferences are not directly input by the user. This is because the variable fixed distances are already associated with the location of the circumference measurements (the fixed distances may have been input at a previous measurement session, or the fixed distances may be estimated based on the inputted height and height-to-length ratio assumptions). If the circumference measurements are taken on or adjacent to readily identifiable reference points (such as illustrated on reference model 64), it is not necessary to measure or input the distance between circumference measurements for each measurement session. As the user inputs circumference data 68, the computer computes sectional volumes for each portion of the body using the previously-described, truncated-cone computation method. The sectional volumes are displayed adjacent to circumference data 68 as shown.

Figure 15:
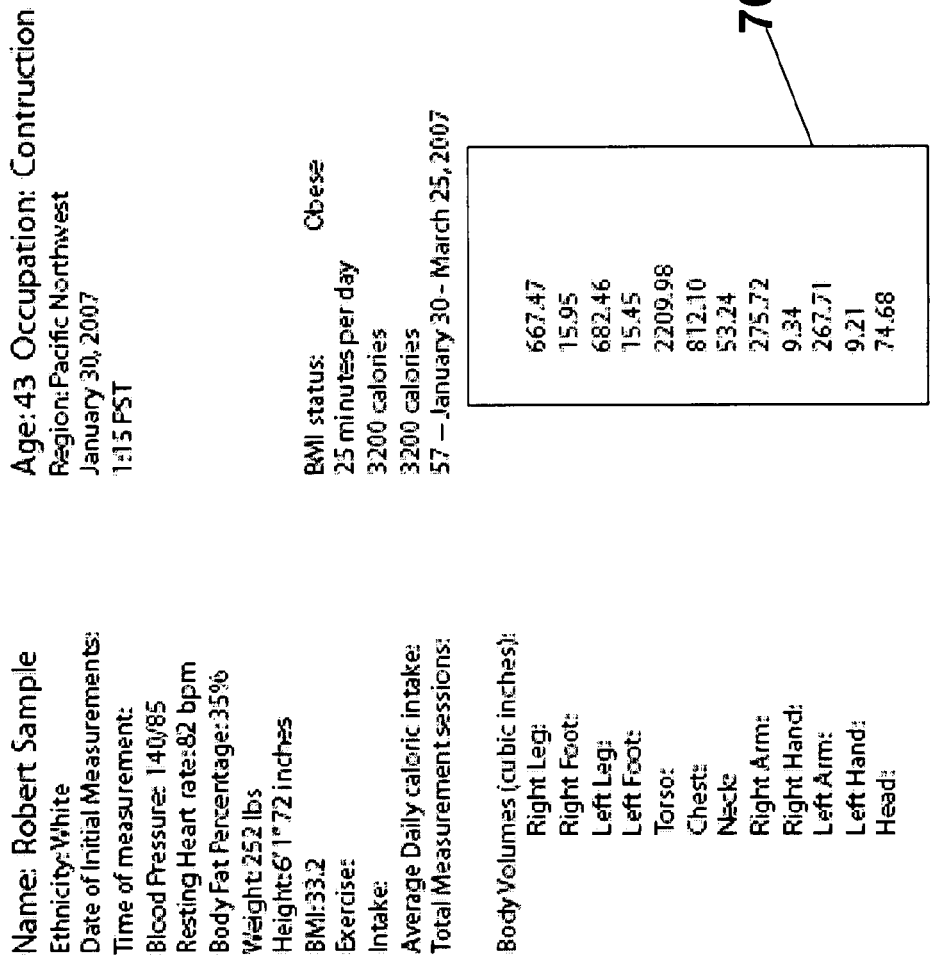
FIG. 15 is a sample report showing a graphical three-dimensional representation of an individual generated by a computer.

Once the data is input into the computer, the computer may be used to generate various helpful reports or displays. One report is illustrated in FIG. 15. This report is a typical format after a first session of measurements. The report shows computed volume data 70 which is computed using circumference data 68 and the inputted or assumed fixed distance data. The health data inputted into the computer in the input display of FIG. 14 is also shown on the report. Most significantly, however, three-dimensional representation 72 is generated and displayed. Three-dimensional representation 72 is a graphical representation of the individual's physical form which takes into account the volume of portions of the individual's body. There are many ways that such a representation may be generated. In the preferred embodiment, a standardized three-dimensional mesh representation or model of a human figure is used as a starting point. Pre-assigned circumference measurements and variable fixed distances are attributed to the standardized model. The individual's unique measurements (circumference measurements and fixed distances) are then used to "refine" the model. For example, if the standardized model has a right bicep with a 15-inch circumference, and the individual has a measured right bicep of 17 inches, the bicep of the standardized model is "expanded" to resemble the individual's bicep. A similar transformation can be used to account for the distances between circumference measurements. For example, length of the standardized model's arms and legs may be lengthened or shortened as necessary to accurately portray the individual's unique physical form. A computer program capable of directing a computer to produce and display these image transformations and manipulations may be readily created by one skilled in the art.

Figure 16:
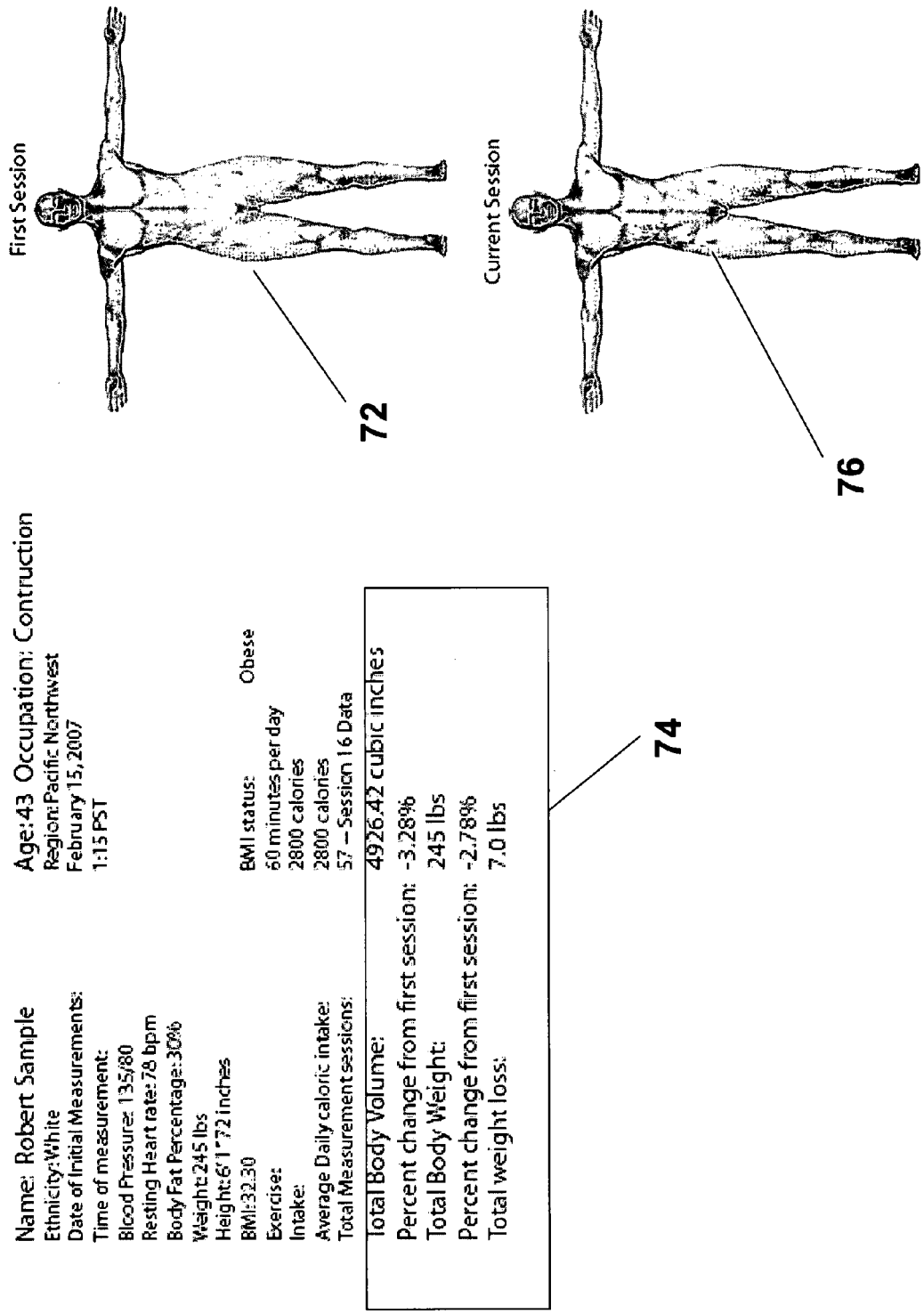
FIG. 16 is a sample report showing changes of the graphical three-dimensional representation of the user generated by a computer.
Figure 17:
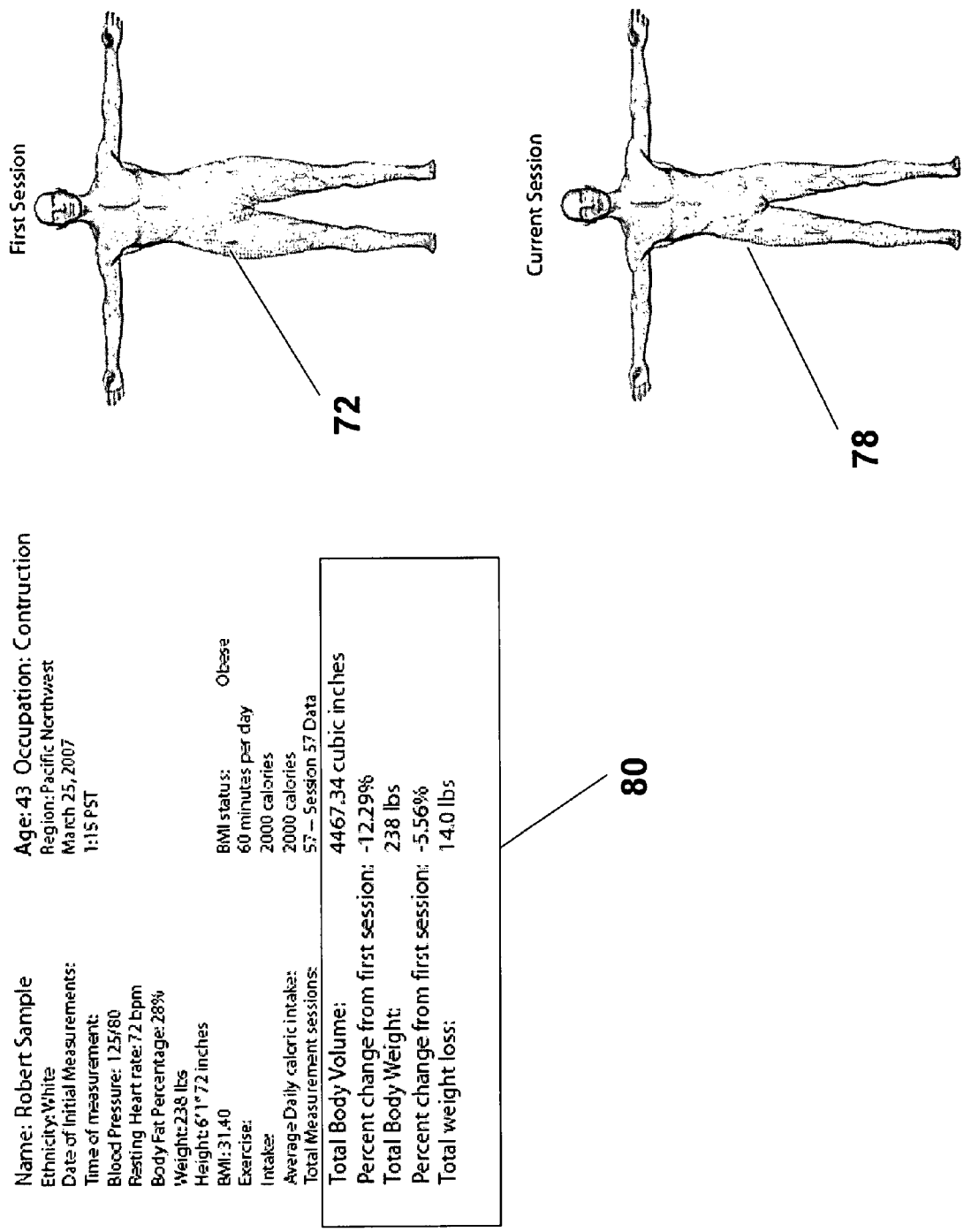
FIG. 17 is a sample report showing changes of the graphical three-dimensional representation of the user generated by a computer.

FIGS. 16 and 17 illustrate reports that may be generated during the course of the individual's exercise or diet program. These reports are created using circumference measurements that are taken and input into the computer in subsequent measurement sessions. As illustrated in FIG. 16, comparison data 74 is provided so that the user can easily appreciate the changes that have occurred since the first measurement session. Comparison data includes the individual's new total body volume, the percentage of body volume change since the first session, the total body weight, the percentage of weight change since the first session, and the total weight loss, changes in percent body fat, resting heart rate and blood pressure. The changes in volume for each portion of the body may also be displayed. The report also displays three-dimensional representation 72 which was generated in the first measurement session next to three-dimensional representation 76 which portrays the individual's current body volume. The reader will appreciate that when presented in this format, the changes in body shape and volume can be readily perceived. This type of feedback is particularly helpful to the individual in understanding the results that have been achieved using the dietary or exercise program.

FIG. 17 is similar to FIG. 16 and illustrates a report generated approximately two months after the first measurement session. Comparison data 80 again illustrates the individual's new total body volume, the percentage of body volume change since the first session, the total body weight, the percentage of weight change since the first session, the total weight loss, changes in percent body, resting heart rate and blood pressure. The report also displays three-dimensional representation 72 which was generated in the first measurement session next to three-dimensional representation 76 which portrays the individual's current body volume. The three-dimensional representations may be shown as a static image (such as is currently illustrated) or as a moving image. For example, the three dimensional representation may rotate slowly along the model's central axis. An animation may also be created and displayed showing the transformation of the individual's body over time as a series of discrete three-dimensional representations shown in succession. One that is skilled in the art would know how to generate these type of graphical illustrations.

The preceding description contains significant detail regarding the novel aspects of the present invention. It is should not be construed, however, as limiting the scope of the invention but rather as providing illustrations of the preferred embodiments of the invention. As an example, the computer interface illustrations are but one type of many possible types well known to those skilled in the art. Thus, the scope of the invention should be fixed by the following claims, rather than by the examples given.

Having described my invention, I claim:

1. A method allowing a user to visualize the volume of at least a chosen portion of a patient to discern the change in said volume over time and thereby determine the efficacy of a dietary or exercise program, comprising:
   a. providing a computer running a computer program;
   b. establishing a first point in time when a first volume for said selected portion is calculated, said volume calculation being made by,
      i. determining an external starting point using a fixed anatomical reference within or adjacent to said chosen portion;
      ii. measuring a first circumference at said external starting point;
      iii. inputting said measurement of said first circumference into said computer program;
      iv. moving a selected first fixed distance along said chosen portion and measuring a second circumference;
      v. inputting said first fixed distance and said measurement of said second circumference into said computer program;
      vi. continuing to move along said chosen portion in a series of variable selected fixed distances, taking a circumference measurement at each stopping point;
      vii. inputting said fixed distances and said measurements of said circumferences into said computer program until the entire length of said chosen portion has been measured;
      viii. using said computer program to compute said volume of said chosen portion at said first point in time by using said recorded fixed distances and circumference measurements taken at said first point in time to compute said volume of said chosen portion as a series of truncated cones;
   c. establishing a second point in time when a second volume for said selected portion is calculated, said volume calculation being made by,
      i. starting at said external starting point used at said first point in time;
      ii. measuring a first circumference at said external starting point;
      iii. inputting said measurement of said first circumference into said computer program;
      iv. moving along said series of variable selected fixed distances to move along said chosen portion;
      v. measuring a series of circumferences corresponding to said series of variable selected fixed distances and inputting said measured circumferences into said computer program;
      vi. using said computer program to compute said volume of said chosen portion at said second point in time by using said recorded fixed distances and circumference measurements taken at said second point in time to compute said volume of said chosen portion as a series of truncated cones;
   d. providing a graphical display associated with said computer;
   e. providing a standard three-dimensional mesh representation of a human figure in said computer program;
   f. attributing pre-assigned circumference measurements and variable fixed distances to said standard three-dimensional mesh representation of a human figure;
   g. substituting said circumferences and said fixed distances actually measured for said patient at said first time for said pre-assigned circumference measurements and variable fixed distances attributed to said standard three-dimensional mesh representation to create a first altered three-dimensional mesh representation;
   h. displaying said first altered three-dimensional mesh representation on said graphical display;
   i. substituting said circumferences and said fixed distances actually measured for said patient at said second time for said pre-assigned circumference measurements and variable fixed distances attributed to said standard three-dimensional mesh representation to create a second altered three-dimensional mesh representation;
   j. displaying said second altered three-dimensional mesh representation on said graphical display;
   k. wherein said computer software includes the ability to present said first altered three-dimensional mesh representations as a moving image wherein an apparent vantage point changes with respect to said first altered three-dimensional mesh representation; and
   l. wherein said computer software includes the ability to present said second altered three-dimensional mesh representations as a moving image wherein an apparent vantage point changes with respect to said second altered three-dimensional mesh representation.

2. The method as recited in claim 1, further comprising:
   a. recording a value at said first point in time selected from a group consisting of the weight of said user, the amount of calories consumed by said user over a period of time, exercise activity performed by said user, the diet of said user, the blood pressure of said user, the resting heart of said user, and the percentage of body fat of said user;
   b. recording a value at said second point in time that is the same value selected at said first point in time; and
   c. using said computer program to display said selected value at said first point in time and said second point in time.

3. The method as recited in claim 1, further comprising the step of determining and recording the body mass index of said user at said first point in time and said second point in time.

4. The method as recited in claim 1, further comprising the step of recording a value selected from as group consisting of: the weight of said user, the amount of calories consumed by said user over a period of time, exercise activity performed by said user, and the diet of said user for said first point in time and said second point in time.

5. A method as recited in claim 1, wherein said computer program computes the difference between said volume computed at said first point in time and said volume computed at said second point in time.

6. A method as recited in claim 5, wherein
   a. said computer is used to record a value selected from a group consisting of the weight of said user, the amount of calories consumed by said user over a period of time, exercise activity performed by said user; and the diet of said user at said first point in time and said second point in time and;
   b. said computer is used to correlate said value to said computed change volume.

7. A method as recited in claim 1, wherein said computer program generates an animation that transforms said first altered three-dimensional mesh representation into said second altered three-dimensional mesh representation over time.

8. A method as recited in claim 1, wherein said selected portion is the entire body of said patient.

* * * * *